US010123959B2

(12) United States Patent
Badalamente et al.

(10) Patent No.: US 10,123,959 B2
(45) Date of Patent: Nov. 13, 2018

(54) METHODS FOR TREATING CELLULITE

(71) Applicant: The Research Foundation for The State University of New York, Albany, NY (US)

(72) Inventors: Marie A. Badalamente, Mt. Sinai, NY (US); Alexander B. Dagum, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/173,092

(22) Filed: Jun. 3, 2016

(65) Prior Publication Data
US 2016/0279046 A1    Sep. 29, 2016

Related U.S. Application Data

(63) Continuation of application No. 11/703,269, filed on Feb. 7, 2007, now abandoned.

(60) Provisional application No. 60/775,690, filed on Feb. 22, 2006.

(51) Int. Cl.
*A61K 38/46* (2006.01)
*A61K 8/66* (2006.01)
*A61K 38/48* (2006.01)
*A61Q 19/06* (2006.01)

(52) U.S. Cl.
CPC ............ *A61K 8/66* (2013.01); *A61K 38/4886* (2013.01); *A61Q 19/06* (2013.01); *A61K 2800/30* (2013.01); *A61K 2800/91* (2013.01)

(58) Field of Classification Search
None
See application file for complete search history.

(56) References Cited

U.S. PATENT DOCUMENTS

| 4,645,668 | A | * | 2/1987 | Pinnell | A61K 38/51 424/94.2 |
| 5,830,741 | A | * | 11/1998 | Dwulet | C12N 5/067 435/183 |
| 6,086,872 | A | * | 7/2000 | Wegman | A61K 38/4886 424/94.1 |
| 6,086,877 | A | * | 7/2000 | Nishioka | A61K 39/3955 424/141.1 |
| 2006/0204488 | A1 | * | 9/2006 | Badalamente | A61K 38/4886 424/94.63 |

OTHER PUBLICATIONS

SurgeryNews.Net, Apr. 2005, pp. 1-3.*
Health News, WebMD, 2006, pp. 1-2.*
Exhibit 1 of the Declaration of Dr. Dagum dated Sep. 4, 2017: "Curriculum Vitae of Alexander B. Dagum, M.D."
Casabona et al., "Microfocused Ultrasound with Visualization and Calcium Hydroxlapatite for Improving Skin Laxity and Cellulite Appearance," PRS Global Open 2017.
Hexsel et al., "Side-By-Side Comparison of Areas with and without Cellulite Depressions Using Magnetic Resonance Imaging," Dermatol. Surg. 2009, 35: 1471-1477.
Omi et al., "Ultrastructural Assessment of Cellulite Morphology: Clues to a Therapeutic Strategy?" Laser Therapy, 2013, 22.2: 131-136.
Friedmann et al., "Cellulite: a Review with a Focus on Subcision," Clin Cosmet Investig Dermatol, 2017, 10: 17-23.
Khan et al., "Treatment of cellulite: Part I. Pathophysiology," J. Am. Acad. Dermatol., 2010, 62(3), 2010: 361-370.
Bell et al., Proteins and Enzymes, at 14 (1988).
Buhren et al., "Hyaluronidase: From Clinical Applications to Molecular and Cellular Mechanisms," Eur. J. Med. Res. vol. 21:5 (2016).
Del Carlo, et al. "Comparative Analysis of Collagen Degradation in Peyronie's Disease Plaque and Dupuytren's Contracture Cord Tissues Injected with Mixed Collagenase Subtypes." The Journal of urology 181.4 (2009): 279.
Querleux et al., "Anatomy and Physiology of Subcutaneous Adipose Tissue by in vivo Magnetic Resonance Imaging and Spectroscopy: Relationships with Sex and Presence of Cellulite," Skin Res. and Technology 8:118-124 (2002).
Denkler et al., "Evidence-Based Medicine: Options for Dupuytren's Contracture: Incise, Excise, and Dissolve," Plastic and Reconstructive Surgery 139(1): 240e-255e (2016).
Endo Pharmaceuticals, "News Release: Endo Announces Positive Data From Phase 2b Study of Collagenase Clostridium Histolyticum (CCH) in Patients with Cellulite," Nov. 17, 2016.
Wanner M et al., "An Evidence-Based Assessment of Treatments for Cellulite," J. Drugs Dermatol. Apr.; 7(4):341-5 (2008).
Green et al., "Cellfina Observations: Pearls and Pitfalls," Seminars in Cutaneous Medicine and Surgery; vol. 34: 144-46 (Sep. 2015).

* cited by examiner

Primary Examiner — Hope Robinson
(74) Attorney, Agent, or Firm — Mayer Brown LLP

(57) ABSTRACT

The invention relates to the discovery that collagenase injections are effective in dissolving and lysing the collagenase septa network in the skin that comprises cellulite. As such, the invention relates to methods of treating cellulite in a patient in need of such treatment comprising injecting or otherwise delivering the effective amount of purified collagenase to the collagenase septa network of cellulite in the skin. The invention also relates to the use of collagenase in the manufacture of a medicament to treat cellulite of the skin.

13 Claims, No Drawings

METHODS FOR TREATING CELLULITE

RELATED APPLICATIONS

This application is a continuation of U.S. application Ser. No. 11/703,269 filed Feb. 7, 2007, now abandoned, which claims priority to U.S. provisional application Ser. No. 60/775,690, filed Feb. 22, 2006, which are incorporated herein by reference in their entirety to the full extend permitted by law. The Assignee of the instant application, The Research Foundation for The State University of New York was a party of a joint research agreement with Biospecifics Technologies, Corp. at the time the invention was made.

GOVERNMENT SUPPORT

The invention was supported, in part, by a grant number RR0101710 from the National Institutes of Health. The U.S. Government has certain rights in the invention.

BACKGROUND OF THE INVENTION

Dimpling of the skin or the "mattress phenomenon" of the thighs and buttocks is commonly referred to as cellulite. This condition is common and appears in otherwise healthy individuals afflicting women much more frequently than men. Over the counter topical therapies abound for the elimination of cellulite. These products and other over the counter topical applications have proved to be useless, costly, and in fact, have never undergone proper placebo controlled clinical trials. Recent randomized, placebo controlled trials of topical retinol and retinol-containing caffeine and ruscogenine have also failed to show merit for the elimination of cellulite.

If the treatment of cellulite is to be successful, then the basic pathophysiology of the condition requires clear definition. It was only in 1998 that Rosenbaum, et al. undertook an investigation of the morphology and biochemistry of cellulite (Rosenbaum, M., Prieto, V., Hellmer, J., Boschmann, M., Krueger, J., Leibel, R. L., Ship, A. G., An Exploratory Investigation of the Morphology and Biochemistry of Cellulite, Plastic & Reconst Surg 101(7): 1934-9, 1998). Seven healthy adult subjects, five women and two men, four affected, three unaffected, underwent sonography of the thigh, measurement of regional in vivo subcutaneous adipose tissue metabolism and full thickness wedge biopsy of the thigh under local anesthesia. The presence of cellulite was defined as evidence of dimpling of the skin of the posterolateral thigh. Any continuous area of skin at least 3 cm in diameter in which no dimpling was evident was designated as unaffected. In all affected individuals studies were performed to include both affected and unaffected areas of the thigh. Microscopic examination of the wedge biopsies and in vivo sonographic examination of the thigh both showed a diffuse pattern of extrusion of underlying adipose tissue into the reticular dermis in affected, but not unaffected, subjects. The study also demonstrated that women had a diffuse pattern of irregular and discontinuous connective tissue immediately below the dermis but the same layer of connective tissue was smooth and continuous in men. This connective tissue layer was more irregular and discontinuous in affected vs. unaffected individuals. No significant differences were noted in subcutaneous adipose tissue morphology, lipolytic responsiveness, or regional blood flow between affected and unaffected sites within individuals. This study demonstrated that there is a sexual dimorphism in the structural characteristics of the dermal connective tissue that pre-disposes women to develop the irregular extrusion of adipose tissue into the dermis which characterized cellulite. This study concluded that there was no evidence of any primary role for adipose tissue physiology, blood flow or adipose tissue biochemistry in the etiology of cellulite but that the connective tissue of the female thigh and buttocks is structured to accentuate differences in small sub-dermal adipose tissue deposits.

This conclusion was substantiated by the work of Pierard, et al. who examined 39 autopsy specimens microscopically (Pierard-Franchimont, C., Pierard G. E., Henry, F., Vroome, V. & Cauwenbergh, G. A Randomized, Placebo-Controlled Trial of Topical Retinol in the Treatment of Cellulite, Amer. J. Clin. Dermatology, 1(6):369-74, 2000). Their control group consisted of four adult women and eleven adult men showing no evidence of cellulite. They state that the lumpy aspect of the dermal hypodermal interface appeared to represent a gender linked (female) characteristic of the thighs and buttocks. Cellulite was identified by this mattress phenomenon microscopically and presented as focally enlarged fibrosclerotic strands partitioning the subcutis. They speculated that these structures might represent a reactive process to sustained hypodermal pressure caused by fat accumulation.

In a more recent study by Querleux, et al. the anatomy and physiology of subcutaneous adipose tissue in relation to sex and the presence of cellulite were studied by in vivo magnetic resonance imaging and spectroscopy (Querleux, B., Cornillon, C., Jolivet, O., Bittoun, J., Anatomy and Physiology of Subcutaneous Adipose Tissue by in vivo Magnetic Resonance Imaging and Spectroscopy: Relationships with Sex and Presence of Cellulite, Skin Research And Tech 8(2):118-124, May 2002). These authors concluded that 3D reconstruction of the fibrous septae network showed a higher percentage of septae in the direction perpendicular to the skin surface in women with cellulite.

There remains no effective treatment of cellulite up to date. It is the object of this invention to provide such methods for treatment of cellulite.

SUMMARY OF THE INVENTION

The invention relates to the discovery that collagenase injections are effective in lysing the collagen septae network of cellulite in humans to treat cellulite and restore a smooth skin appearance. The invention relates to methods of treating cellulite in a subject in need of such treatment, which involves injecting an effective amount of purified collagenase, and in the manufacture of a medicament to treat cellulite. The collagenase is preferably purified and substantially free of other enzymes, such as proteases and/or hyaluronidase.

DETAILED DESCRIPTION OF SPECIFIC EMBODIMENTS

The invention relates to the discovery that collagenase injections are effective in lysing the collagen septae network of cellulite in humans to treat cellulite and restore a smooth skin appearance. The invention relates to methods of treating cellulite in a subject in need of such treatment, which involves injecting an effective amount of collagenase to the thigh and/or buttocks. The invention also relates to the use of collagenase in the manufacture of a medicament to treat cellulite.

Collagenase injections have been proposed for the treatment of diseases such as Dupuytren's disease, adhesive capsulitis, and Peyronie's disease. These diseases are all associated with collagen cords or plaques. (Wegman, Thomas L. U.S. Pat. No. 5,589,171 issued on Dec. 31, 1996, U.S. Pat. No. 6,086,872 issued on Jul. 11, 2000, U.S. Pat. No. 6,022,539, issued on Feb. 8, 2000, Adhesive Capsulitis-patent pending, all of which are incorporated herein by reference in their entirety).

Collagenase injections have also been proposed for the treatment of cellulite when combined with hyaluronidase, a soluble enzyme product prepared from mammalian testes (see Pinnell, Sheldon R., U.S. Pat. No. 4,645,668, issued on Feb. 24, 1987). The patent disclosed one working example for cellulite with a low dose of collagenase (100 units) in combination with hyaluronidase (150 units) for only one female patient. No further details in the improvement of cellulite after the injections were presented.

The use of intralesional injection of purified Clostridial collagenase has been shown to be clinically safe and effective in clinical trials in Dupuytren's disease in correcting the flexion contracture deformity of the hand(s). Additionally, the use of extracapsular injection of purified Clostridial collagenase has been shown to be clinically safe and effective in the treatment of adhesive capsulitis (frozen shoulder) in clinical trials. A restoring injection has also been used by others in clinical trials in Peyronie's disease, a contracture deformity of the penis.

The published work of the inventor, Dr. Badalamente, in Dupuytren's disease forms the rationale for the proposed invention (Starkweather, K., Lattuga, S., Hurst, L. C., Badalamente, M. A., Guilak, F., Sampson, S. P., Dowd, A., Wisch, D. Collagenase in the Treatment of Dupuytren's Disease: An in vitro Study, J. Hand Surg. 21(3):490-95, 1996; Badalamente, M. A., Hurst, L. C., Enzyme Injection as a Nonoperative Treatment for Dupuytren's Disease, J. Drug-Delivery 3(1):35-40, 1996; Hurst, L. C., Badalamente, M. A. (invited authorship) Nonoperative Treatment of Dupuytren's Disease, Hand Clinics, G. M. Rayan (ed). W. B. Saunders 15(1), 97-107, 1999; Hurst, L. C., Badalamente, M. A. (invited editors & authorship), Dupuytren's Disease, E. Mackin, R. Tubiana, C. Leclercq, L. C. Hurst, M. A. Badalamente (eds), Martin Dunitz Publisher, London (2000); Badalamente, M. A., Hurst, L. C. Enzyme Injection as a Nonsurgical Treatment of Dupuytren's Disease, J. Hands Surg. 25(4); 629-36, 2000; Badalamente, M. A., Hurst, L. C., Hentz, V. R. Collagen as a Clinical Target: Nonoperative Treatment of Dupuytren's Disease, J. Hand Surg. 27A(5):788-98, 2002). In Dupuytren's disease, the pathognomonic fibrous cord is often interspersed with a septa-like arrangement of adipose tissue. These present clinically as mattress-type "lumps" of varying sizes and in Dupuytren's disease, are termed nodules. There has been a consistent clinical finding in both Phase 2 and 3 trials for Dupuytren's disease that after purified Clostridial collagenase injection, not only does the collagenous cord dissolve and rupture when subjected to pressure in extension, but the fibro-fatty nodules, also resolve, and harmlessly resorb. Therefore, collagenase injected subcutaneously into an area of cellulite was postulated to be a safe and effective treatment for this condition in restoring a smooth appearance of the skin of the thighs and/or buttocks.

Collagenase is an enzyme that has specific ability to digest collagen. A preferred form of collagenase is derived from the fermentation of *Clostridium histolyticum* and is purified by a chromatographic technique, such as that disclosed in U.S. Application Ser. No. 60/763,470 filed on Jan. 30, 2006, which is incorporated herein by reference. Collagenase naturally produced by *Clostridium histolyticum*-once purified will exhibit two distinct peaks when run on an electrophoresis SDS gel. It is these two distinct peaks that are referred to as collagenase I and collagenase II.

Sterilized lyophilized collagenase powder is commercially available having a minimum assay of 50 units per mg. The assay may range considerably above that from batch to batch, but is taken into account in determining the weight of the powder to use with a pharmaceutically acceptable carrier, for example, normal saline, in preparing a desired concentration for treatment.

The collagenase is applied in a liquid carrier that is pharmaceutically acceptable, including inertness towards the collagenase. Examples are normal saline, aqueous, NaCl/CaC12 buffer, aqueous dextran solution, aqueous hetastarch solution.

One form of the Purified Collagenase used for Injection, is comprised of two microbial collagenases, referred to as "Collagenase ABC I" and "Collagenase ABC II". Both collagenases are isolated and purified from the fermentation of the bacterium *Clostidium histolyticum* and belong to the same metalloprotease.

Collagenase ABC I is a single polypeptide chain consisting of approximately 1000 amino acids of known sequence. It has an observed molecular weight of 115 kiloDalton (kD), an isoelectric point (pI) between 5.63-5.68 and an extinction coefficient of 1.480. From its activity behavior toward synthetic substrate, it has been determined that Collagenase ABC I is the class I *Clostidium histolyticum* collagenase in the literature.

Collagenase ABC II is also a single polypeptide chain consisting of about 1000 amino acids of deduced sequence. It has an observed molecular weight of 110 kD, an isoelectric point between 5.46-5.57 and an extinction coefficient of 1.576. Collagenase ABC II functionally belongs to the class II *Clostidium histolyticum* collagenase in the literature.

The drug substance may have a 1 to 1 mass ratio of collagenase ABC-I and ABC-II with an extinction coefficient of 1.528. Both collagenases require tightly bound zinc and loosely bound calcium for their activity. Collagenase ABC I and Collagenase ABC II are not immunologically cross-reactive and have a very broad hydrolyzing reactivity toward all types of collagen. Even though each collagenase shows different specificity, together they provide synergistic activity toward collagen.

Lyophilized Collagen for Injection is purified clostridial collagenase prepared as lyophilized formulation and may contain about 0.1 mg lactose monohydrate USP per 1,000 ABC units of collagenase activity.

A preferred collagenase composition comprises a mixture of collagenase I and collagenase II in a mass ratio of about 1 to 1 and has specific activity from about 500 SRC units/mg to about 15,000 SRC units/mg, preferably of at least about 700 SRC units/mg, more preferably of at least about 1000 SRC units/mg, even more preferably at least about 1500 SRC units/mg. One SRC unit will solubilize rat tail collagen into ninhydrin reaction material equivalent to 1 nanomole of leucine per minute, at 25 degrees C., pH 7.4. Collagenase has been described in ABC units as well. The potency assay of collagenase is based on the digestion of undenatured collagen (from bovine tendon) at pH 7.2 and 37 degrees C. for 20-24 hours. The number of peptide bonds cleaved are measured by reaction with ninhydrin. Amino groups released by a solubilize digestion control are subtracted. One net ABC unit of collagenase will solubilize ninhydrin reactive material equivalent to 1.09 nanomoles of leucine per minute. One SRC unit equals approximately 6.3 ABC units.

The collagenase is preferably administered via injection in a liquid carrier that is pharmaceutically acceptable. Preferably, the carrier does not interact or deactivate the collagenase. Examples are normal saline, aqueous NaCl/CaCl$_2$, buffer (containing 0.9% NaCl and 2 mM CaC12). For example, the lyophilized formulation can contain 0.1 mg lactose monohydrate per 1,000 ABC units. Each glass vial used below contained 5,150 ABC units collagenase.

In accordance with the invention, collagenase in a liquid carrier is injected into an area of cellulite in the subject's posterolateral thigh. The amount and concentration of collagenase used is effective to lyse and dissolve the collagen septa network of the cellulite.

The injection is a sterile one and does not exceed 1.0 ml. The total dosage is injected at five different points into the posterolateral thigh where the cellulite dimples of the thigh are most apparent. The objective is to assure good distribution of the collagenase. Patients preferably rest on the contra lateral thigh, in bed, for about one, preferably two hours or more.

In other embodiments, the collagenase can be administrated locally or topically, such as, a transdermal patch or topical cream or topical ointment to the area of cellulite or can be administered via an implant, such as, microcapsules or microspheres which release collagenase over time.

In one embodiment, the patient is characterized as having an area of at least 10×10 cm of cellulite on the posterolateral thigh. The invention can achieve improvement in restoring normal and smooth skin appearance in the 10×10 cm area of cellulite on the posterolateral thigh.

In another embodiment of the present invention, collagenase can be administrated locally or topically, such as, a transdermal patch or topical cream or topical ointment to the area of cellulite or can be administered via an implant, such as, microcapsules or microspheres which release collagenase over time and is administered in the absence of triamcinolone or other corticosteroids.

In cases where results of a single treatment are considered inadequate, the same procedures, total amount of collagenase and concentration may be repeated at 4-6 weeks intervals. Areas of cellulite, other than the posterolateral thigh may also require treatment, or repeated treatment at 4-6 week intervals. For example, the front of the thigh and the buttocks may contain areas of cellulite.

Experimental

Methods

Ten patients entered the study protocol, all females, mean age 41±10 years. The mean body mass index (BMI) was 28.

The minimum area of cellulite of the posterolateral thigh needed for inclusion was 10×10 cm. All patients had areas of cellulite of the posterolateral thigh which exceeded the minimum 10×10 cm area. Baseline digital photographs were taken of the treatment area. In a sterile fashion, 10,000 ABC units (0.58 mg) were injected at five points in the 10×10 cm target cellulite area. The total fluid volume of the injection was 1.0 ml. The buffer used was sterile 0.9% NaCl and 2 mM CaC12. All patients were followed post injection, at one day, one week, one, three, and six months. Post treatment photographs were taken serially.

Patients had the option of choosing to have a similar collagenase injection on the opposite side, for cosmetic symmetry, when they reached the time interval of 6 months post the first collagenase injection. Qualification of the reduction/elimination of cellulite in the target area of the thigh was by visual inspection and photographic documentation.

The target area of the cellulite treated was divided into four equal quadrants in the 10×10 cm target treatment area. Reduction/elimination of cellulite in the target treatment area was quantified by visual inspection by quadrant, e.g., 4/4=all quadrants responded to treatment, 3/4=three quadrants responded to treatment, 2/4 two quadrants responded to treatment, 1/4=one quadrant responded to treatment, 0/4=no quadrants responded to treatment. The actual area in cm$^2$ of any remaining cellulite of the posterolateral target area of cellulite was also measured. Photographs were also used for documentation.

Results:

All patients experienced a reduction in cellulite of the target thigh after collagenase injection. Table 1 shows the results of the reduction in the cellulite in the quadrants of the thighs in the patients treated. There was significant reduction in cellulite appearance of the injected area. Cellulite was reduced by 77% by day 1 in comparison to baseline. This result was sustained in the longer term. In comparison to baseline, cellulite area was reduced by 74% at 1 week, by 89% at 1 month, by 86% at 3 months and by 76% at 6 months.

Adverse events included tenderness in the injection area, ecchymosis and mild edema which resolved well in the mean of 10, 18 and 6 days respectively.

Significant improvement in the reduction of cellulite of the posterolateral thigh was seen in the patients who received collagenase injection(s). This study has shown that collagenase injection of areas of cellulite is a safe and effective method.

While this invention has been particularly shown and described with reference to preferred embodiments thereof, it will be understood by those skilled in the art that various changes in form and details may be made therein without departing from the scope of the invention encompassed by the appended claims.

TABLE 1

| Patient | Age | Sex | Thigh | Parameters | Baseline | 1 day post 1st | 1 week post 1st | 1 month post 1st | 3 month post 1st | 6 month post 1st |
| --- | --- | --- | --- | --- | --- | --- | --- | --- | --- | --- |
| LY C-009 | 37 | F | Right | BMI | 33 | 33 | 34 | 34 | 34 | 36 |
| | | | | circumference: | 68 cm | 68 cm | 68 cm | 68 cm | 68 cm | 69 cm |
| | | | | Area (cm): | 12 × 14 cm | 12 × 14 cm | 5 × 5 cm | 5 × 5 cm | 5 × 5 cm | 8 × 9 cm |
| | | | | Quadrants | 4 | 4 | 2 | 2 | 2 | 3 |

| Patient | Age | Sex | Thigh | Parameters | Baseline | 1 day post 2nd | 1 week post 1st | 1 month post 1st | 3 month post 1st | 6 month post 1st |
| --- | --- | --- | --- | --- | --- | --- | --- | --- | --- | --- |
| NW C-001 | 52 | F | Right | BMI (cm) | 32 | 31 | 31 | 31 | 32 | 32 |
| | | | | circumference: | 68 cm | 66 cm | 64 cm | 64 cm | 64 cm | 64 cm |

TABLE 1-continued

| | | | | | Area (cm): | 16 × 12 cm | 2 × 2 cm | 5 × 5 cm | 0 | 5 × 1 cm | 5 × 1 cm |
| | | | | | Quadrants | 4 | 1 | 2 | 0 | 1 | 1 |

| Patient | Age | Sex | Thigh | Parameters | Baseline | 1 day post 2nd | 1 week post 2nd | 1 month post2nd | 3 month post 2nd | 6 month post 2nd |
|---|---|---|---|---|---|---|---|---|---|---|
| NW C-001 | 52 | F | Left | BMI (cm) | 32 | 32 | 32 | 32 | 31 | 30 |
| | | | | circumference: | 68 cm | 68 cm | 69 cm | 66 cm | 63 cm | 63 cm |
| | | | | Area (cm): | 19 × 19 cm | 19 × 19 cm | 5 × 5 cm | 0 | 4 × 0 cm | 0 |
| | | | | Quadrants | 4 | 4 | 2 | 0 | 1 | 0 |

| Patient | Age | Sex | Thigh | Parameters | Baseline | 1 day post 1st | 1 week post 1st | 1 month post 1st | 3 month post 1st | 6 month post 1st |
|---|---|---|---|---|---|---|---|---|---|---|
| PD C-004 | 44 | F | Left | BMI (cm) | 24 | 24 | 25 | 24 | 25 | 25 |
| | | | | circumference: | 57 | 65 | 66 | 63 | 56 | 56 |
| | | | | Area (cm): | 10 × 10 | 0 | 0 | 4 × 3 | 4 × 3 | 4 × 3 |
| | | | | Quadrants | 4 | 0 | 0 | 1 | 1 | 1 |

| Patient | Age | Sex | Thigh | Parameters | Baseline | 1 day post 2nd | 1 week post 2nd | 1 month post2nd | 3 month post 2nd | 6 month post 2nd |
|---|---|---|---|---|---|---|---|---|---|---|
| PD-C-004 | 44 | F | Right | BMI (cm) | 25 | 25 | 25 | 25 | 25 | |
| | | | | circumference: | 60 | 62 | 62 | 62 | 62 | |
| | | | | Area (cm): | 10 × 10 | 0 | 1 × 4 | 0 | 0 | |
| | | | | Quadrants | 4 | 0 | 1 | 0 | 0 | |

| Patient | Age | Sex | Thigh | Parameters | Baseline | 1 day post 1st | 1 week post 1st | 1 month post 1st | 3 month post 1st | 6 month post 1st |
|---|---|---|---|---|---|---|---|---|---|---|
| AP C-012 | 54 | F | Right | BMI (cm) | 23 | 23 | 23 | 23 | Lost to follow up | |
| | | | | circumference: | 56 | 56 | 56 | 52 | | |
| | | | | Area (cm): | 10 × 11 | 3 × 9 | 3 × 5 | 5 × 4 | | |
| | | | | Quadrants | 4 | 2 | 1 | 1 | | |
| ER-C-015 | 44 | F | Left | BMI (cm) | 22 | 22 | 22 | 22 | 21 | |
| | | | | circumference: | 51 | 54 | 52 | 53 | 53 | |
| | | | | Area (cm): | 10 × 10 | 5 × 9 | 4 × 10 | 0 | 0 | |
| | | | | Quadrants | 4 | 2 | 3 | 0 | 0 | |
| AE C-016 | 40 | F | Right | BMI (cm) | 31 | 31 | 31 | 31 | 31 | 30 |
| | | | | circumference: | 67 | 79 | 72 | 69 | 68 | 64 |
| | | | | Area (cm): | 12 × 12 | 0 | 9 × 5 | 2 × 3 | 2 × 7 | 2 × 7 |
| | | | | Quadrants | 4 | 0 | 3 | 1 | 2 | 2 |

| Patient | Age | Sex | Thigh | Parameters | Baseline | 1 day post 2nd | 1 week post 2nd | 1 month post2nd | 3 month post 2nd | 6 month post 2nd |
|---|---|---|---|---|---|---|---|---|---|---|
| AE C-016 | 40 | F | Left | BMI (cm) | 31 | 31 | 31 | 31 | 31 | |
| | | | | circumference: | 69 | 71 | 68 | 68 | 68 | |
| | | | | Area (cm): | 12 × 14 | 0 | 2 × 4 | 1 × 2 | 0 | |
| | | | | Quadrants | 4 | 0 | 1 | 1 | 0 | |

| Patient | Age | Sex | Thigh | Parameters | Baseline | 1 day post 1st | 1 week post 1st | 1 month post 1st | 3 month post 1st | 6 month post 1st |
|---|---|---|---|---|---|---|---|---|---|---|
| MM C-017 | 27 | F | Right | BMI (cm) | 37 | 37 | 37 | 37 | Lost to Follow up | |
| | | | | circumference: | 74 | 74 | 74 | 74 | | |
| | | | | Area (cm): | 14 × 14 | 0 | 1 × 10 | 6 × 3 | | |
| | | | | Quadrants | 4 | 0 | 2 | 1 | | |

What is claimed is:

1. A method of treating cellulite in a subject in need thereof, comprising the steps of (a) providing a composition consisting essentially of a mixture of purified collagenase I and II in a mass ratio of about 1:1 obtained from *Clostridium histolyticum*, wherein the mixture has a specific activity of at least 10,000 ABC units per 0.58 mg of collagenase I and II, and (b) injecting the composition to a collagenous septa network of cellulite at a dose of at least 0.18 mg of the mixture of purified collagenase I and II.

2. The method according to claim 1, wherein the mixture of purified collagenase I and II is injected in an absence of triamcinolone or other corticosteroids.

3. The method according to claim 1, wherein the dose of purified collagenase I and II is at least 0.25 mg.

4. The method according to claim 1, wherein the dose of purified collagenase I and II is at least 0.36 mg.

5. The method according to claim 1, wherein the dose of purified collagenase I and II is at least 0.58 mg.

6. The method according to claim 1, wherein the composition further consists essentially of a pharmaceutically acceptable carrier.

7. The method according to claim 1, wherein the mixture of purified collagenase I and II is injected at multiple sites.

8. The method according to claim 1, wherein the injection is delivered in the area of cellulite, characterized by skin dimpling.

9. The method according to claim 1, wherein the subject is a human patient.

10. The method according to claim 1, wherein the treatment is repeated after about four to six weeks.

11. The method according to claim 1, wherein the composition is administered to a population of human subjects and after one month of receiving at least one administration of the mixture of purified collagenase I and II, at least 89% of the subjects achieve a significant visual reduction in the appearance of cellulite quantified by visual inspection by quadrant in comparison to baseline.

12. The method according to claim 1, wherein the dose of purified collagenase I and II is at least 0.55 mg.

13. The method according to claim 1, wherein the dose of purified collagenase I and II is at least 5.48 mg.

* * * * *

UNITED STATES PATENT AND TRADEMARK OFFICE
CERTIFICATE OF CORRECTION

PATENT NO. : 10,123,959 B2
APPLICATION NO. : 15/173092
DATED : November 13, 2018
INVENTOR(S) : Marie A. Badalamente and Alexander B. Dagum Page 1 of 1

It is certified that error appears in the above-identified patent and that said Letters Patent is hereby corrected as shown below:

In the Specification

- Column 1, Lines 18-20, "The invention was supported, in part, by a grant number RR0101710 from the National Institutes of Health. The U.S. Government has certain rights in the invention." should read "This invention was made with government support under RR010710 awarded by the National Institutes of Health. The government has certain rights in the invention."

Signed and Sealed this
Thirtieth Day of April, 2019

Andrei Iancu
*Director of the United States Patent and Trademark Office*